United States Patent
Adinolfi et al.

(10) Patent No.: US 11,925,387 B2
(45) Date of Patent: Mar. 12, 2024

(54) SURGICAL ACCESS DEVICE WITH FASCIAL CLOSURE SYSTEM

(71) Applicant: Covidien LP, Mansfield, MA (US)

(72) Inventors: Amanda Adinolfi, Wallingford, CT (US); Oksana Buyda, Northford, CT (US); Krishnakumar Somasundaram, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/862,899

(22) Filed: Jul. 12, 2022

(65) Prior Publication Data

US 2022/0346835 A1  Nov. 3, 2022

Related U.S. Application Data

(63) Continuation of application No. 16/550,470, filed on Aug. 26, 2019, now Pat. No. 11,389,193.

(60) Provisional application No. 62/739,909, filed on Oct. 2, 2018.

(51) Int. Cl.
    *A61B 17/34*     (2006.01)
    *A61B 17/00*     (2006.01)
    *A61B 17/04*     (2006.01)

(52) U.S. Cl.
    CPC ...... *A61B 17/3423* (2013.01); *A61B 17/0469* (2013.01); *A61B 17/0057* (2013.01); *A61B 2017/3429* (2013.01)

(58) Field of Classification Search
    CPC .................................................. A61B 17/3423
    See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |

(Continued)

FOREIGN PATENT DOCUMENTS

| | | |
|---|---|---|
| CA | 2702419 A1 | 11/2010 |
| EP | 0226026 A2 | 6/1987 |

(Continued)

OTHER PUBLICATIONS

Extended European Search Report dated Nov. 20, 2019 issued in corresponding EP Appln. No. 19200769.8.

*Primary Examiner* — Nicholas W Woodall
(74) *Attorney, Agent, or Firm* — Carter, DeLuca & Farrell LLP

(57) ABSTRACT

A surgical access device is disclosed and includes a housing, a cannula, a guide, and an expandable member. The cannula extends distally from the housing and defines a longitudinal axis. A wall of the cannula includes a first slot defined therein. The guide is engagable with the housing and defines a first channel. The first channel is disposed at a non-parallel angle relative to the longitudinal axis. The expandable member is disposed adjacent a distal portion of the cannula and is transitionable between a collapsed configuration and an expanded configuration. A first surgical instrument is insertable through the first channel of the guide and through the first slot of the cannula.

20 Claims, 10 Drawing Sheets

(56) References Cited

U.S. PATENT DOCUMENTS

| | | |
|---|---|---|
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,716,329 A * | 2/1998 | Dieter .................... A61B 1/303 600/184 |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |

(56) References Cited

U.S. PATENT DOCUMENTS

| | | |
|---|---|---|
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |

(56) References Cited

U.S. PATENT DOCUMENTS

| | | |
|---|---|---|
| 8,585,632 B2 | 11/2013 | Okoniewski |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0130559 A1* | 7/2003 | Morin .................. A61B 1/31 600/128 |
| 2003/0187376 A1 | 10/2003 | Rambo |
| 2003/0233115 A1 | 12/2003 | Eversull et al. |
| 2003/0236544 A1 | 12/2003 | Lunsford et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0009797 A1 | 1/2006 | Armstrong |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0005647 A1 | 1/2009 | Bozdag |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0062872 A1* | 3/2009 | Chin .................. A61B 1/00082 606/86 R |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0080523 A1 | 4/2010 | Lesvigne et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0040324 A1 | 2/2011 | McCarthy et al. |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087075 A1 | 4/2011 | Wenchell et al. |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0116303 A1 | 5/2012 | Marx |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |

(56) References Cited

U.S. PATENT DOCUMENTS

| | | |
|---|---|---|
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0038793 A1 | 2/2015 | Prior et al. |
| 2015/0335320 A1 | 11/2015 | Keating et al. |
| 2018/0271557 A1 | 9/2018 | Buyda et al. |
| 2019/0223905 A1 | 7/2019 | Zeller |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 3225202 | 10/2017 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 A1 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008112364 | 9/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2013105993 A2 | 7/2013 |

* cited by examiner

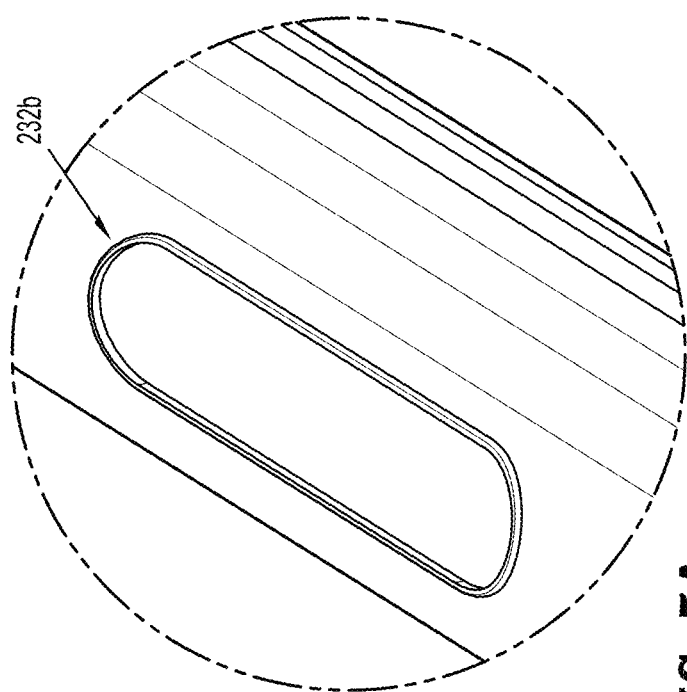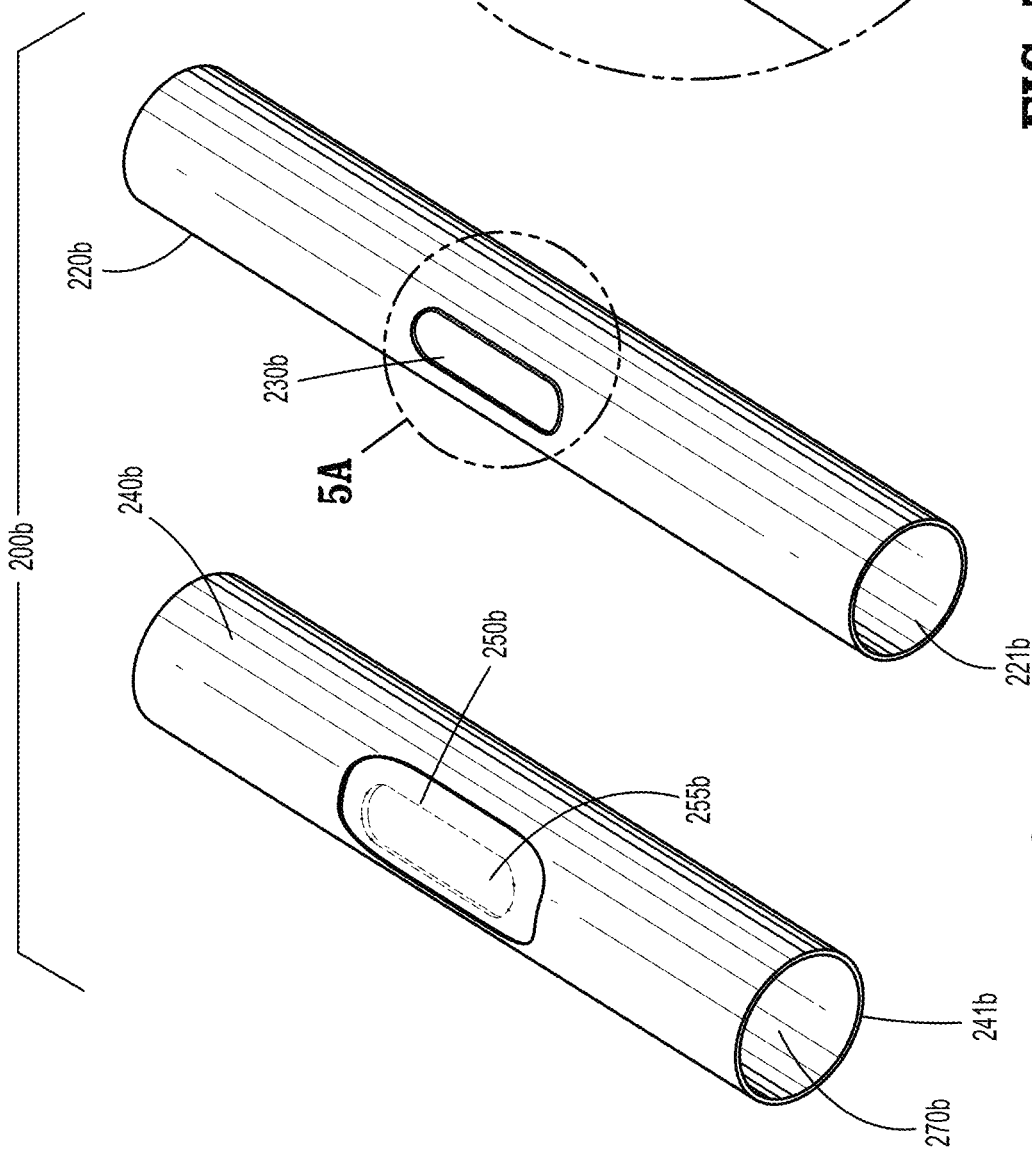
FIG. 5A
FIG. 5

SURGICAL ACCESS DEVICE WITH FASCIAL CLOSURE SYSTEM

CROSS-REFERENCE TO RELATED APPLICATIONS

This application is a continuation of U.S. patent application Ser. No. 16/550,470, filed on Aug. 26, 2019, which claims the benefit of and priority to U.S. Provisional Patent Application Ser. No. 62/739,909 filed Oct. 2, 2018, the entire contents of each of which being incorporated by reference herein.

BACKGROUND

The present disclosure relates to a surgical apparatus. More particularly, the present disclosure relates to a surgical access device that can maintain its position relative to the patient during a surgical procedure. The surgical access device also includes a system to facilitate fascial closure.

In minimally invasive surgical procedures, including endoscopic and laparoscopic surgeries, a surgical access device permits the introduction of a variety of surgical instruments into a body cavity. A surgical access device (e.g., a cannula) is introduced through an incision in tissue to provide access to an underlying surgical site in the body. The cannula is introduced through the incision with an obturator disposed in the passageway of the cannula. The obturator can have a blunt or sharp tip for penetrating tissue. The obturator is removed to permit introduction of surgical instrumentation through the surgical access device to perform the surgical procedure.

These procedures are performed while the abdominal cavity is inflated with a pressurized gas. To maintain the position of the surgical access device with respect to the body wall, the access device can include an anchor near its distal end. To help maintain the position of the surgical access device with respect to the body wall, an inflatable balloon disposed near a distal end of the surgical access device can be used. The access device is positioned so that the balloon is disposed inside the patient's body, anchoring the access device. Inflating such a balloon while the surgical access device is within the body helps prevent the surgical access device from undesired movement with respect to the body.

Additionally, following such surgical procedures, the incision is closed. A suture and needle is used to close the fascia and other tissue, using a separate instrument. It may be helpful to provide a single surgical access device that can be maintained in its position relative to the body, and that can allow a device to pass therethrough to close the incision. It may also be helpful to provide a single surgical access device that can be maintained in its position without the need to remove the surgical access device and/or desufflate the working space prior to facial closure.

SUMMARY

The present disclosure relates to a surgical access device including a housing, a cannula, a guide, and an expandable member. The cannula extends distally from the housing and defines a longitudinal axis. A wall of the cannula includes a first slot defined therein. The guide is engagable with the housing and defines a first channel. The first channel is disposed at a non-parallel angle relative to the longitudinal axis. The expandable member is disposed adjacent a distal portion of the cannula and is transitionable between a collapsed configuration and an expanded configuration. A first surgical instrument is insertable through the first channel of the guide and through the first slot of the cannula.

In disclosed embodiments, the wall of the cannula may include a second slot defined therein. The second slot may be longitudinally offset from the first slot.

It is also disclosed that the cannula may include an inner tube and an outer tube. It is also disclosed that the inner tube may define the first slot, and the outer tube may define an outer tube slot. The first slot and the outer tube slot may be aligned with each other. In embodiments, the surgical access device may include a film covering at least one of the first slot and the outer tube slot. It is further disclosed that the film may be adhered to a recessed surface of at least one of the inner tube and the outer tube.

In embodiments of the present disclosure, the surgical access device may include at least one channel disposed within the wall of the cannula. It is further disclosed that the at least one channel may extend between a proximal portion of the cannula and the distal portion of the cannula, and that the at least one channel may be radially offset from the first slot.

In disclosed embodiments, the expandable member may include a fixation mesh or a balloon fixation device.

It is further disclosed that in embodiments where the cannula includes an inner tube and an outer tube, the expandable member may include a balloon fixation device. It is also disclosed that the housing may include an inflation port disposed in fluid communication with the balloon fixation device. It is further disclosed that there may be a space between the inner tube and the outer tube that is disposed in fluid communication with the inflation port and with the balloon fixation device.

The present disclosure also relates to a method of performing a surgical procedure including inserting a portion of a cannula through an incision in a patient, transitioning an expandable member of the cannula from a collapsed configuration to an expanded configuration, inserting a first surgical instrument along a longitudinal axis through an aperture of the cannula, performing a surgical task with the first surgical instrument, inserting a second surgical instrument along a second axis which is disposed at a non-parallel angle relative to the longitudinal axis, inserting a distal tip of the second surgical instrument through a slot within a wall of the cannula, and performing a surgical task with the second surgical instrument.

In disclosed embodiment, the method may include removing the first surgical instrument from the aperture of the cannula prior to inserting the second surgical instrument along the second axis.

It is further disclosed that the method may include urging the distal tip of the second surgical instrument through a film covering the slot within the wall of the cannula.

Additionally, the method may include transitioning the expandable member of the cannula from the expanded configuration to the collapsed configuration.

BRIEF DESCRIPTION OF THE DRAWINGS

Various embodiments of the present disclosure are illustrated herein with reference to the accompanying drawings, wherein:

FIG. 5 is a perspective view of an inner tube and an outer tube of the surgical access device of FIGS. 1-3 in accordance with another embodiment of the present disclosure;

FIG. 5A is an enlarged view of the area of detail indicated in FIG. 5;

DETAILED DESCRIPTION

Figure 1:
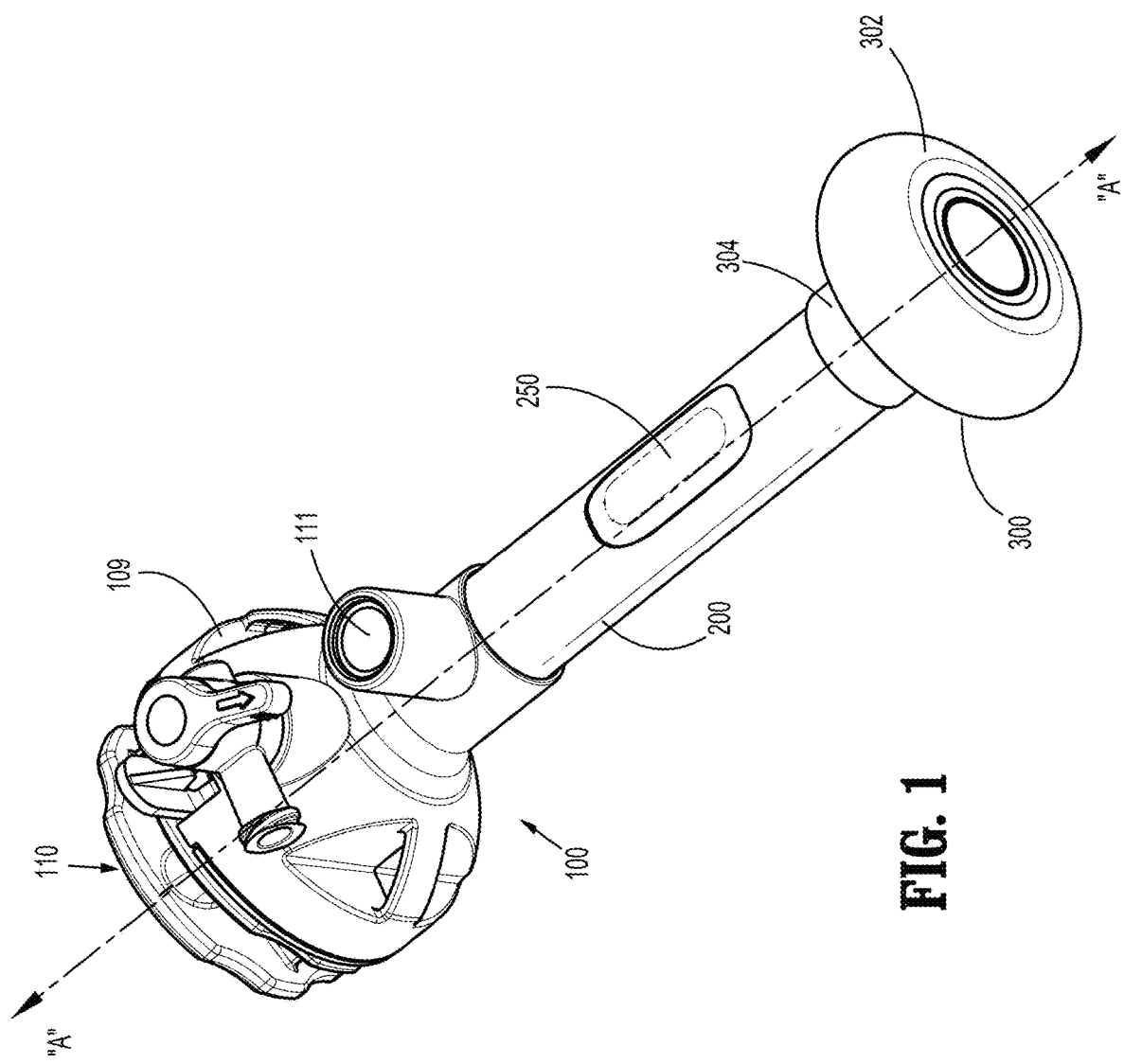
FIG. 1 is a perspective view of a surgical access device including a balloon fixation device of the present disclosure.

Embodiments of the presently disclosed surgical access device are described in detail with reference to the drawings, wherein like reference numerals designate corresponding elements in each of the several views.

Various embodiments of a surgical access device are described herein. Generally, the surgical access devices include a fixation device (e.g., a balloon fixation device or a fixation mesh device) configured to engage tissue to help maintain the surgical access device in its position relative to the body during use, and include a fascial closure system which creates an efficient way of closing the incision through which the surgical access device entered the body. FIGS. 1-6 illustrate embodiments of a surgical access device including a balloon fixation device, and FIGS. 7-10 illustrate embodiments of a surgical access device including a fixation mesh device. It is envisioned that the surgical access devices disclosed herein are useful in Hasson techniques, as well as those using blunt, bladeless, bladed and/or optical obturators where the surgical access device is used to gain entry to the abdomen for laparoscopy, for example.

Figure 1A:
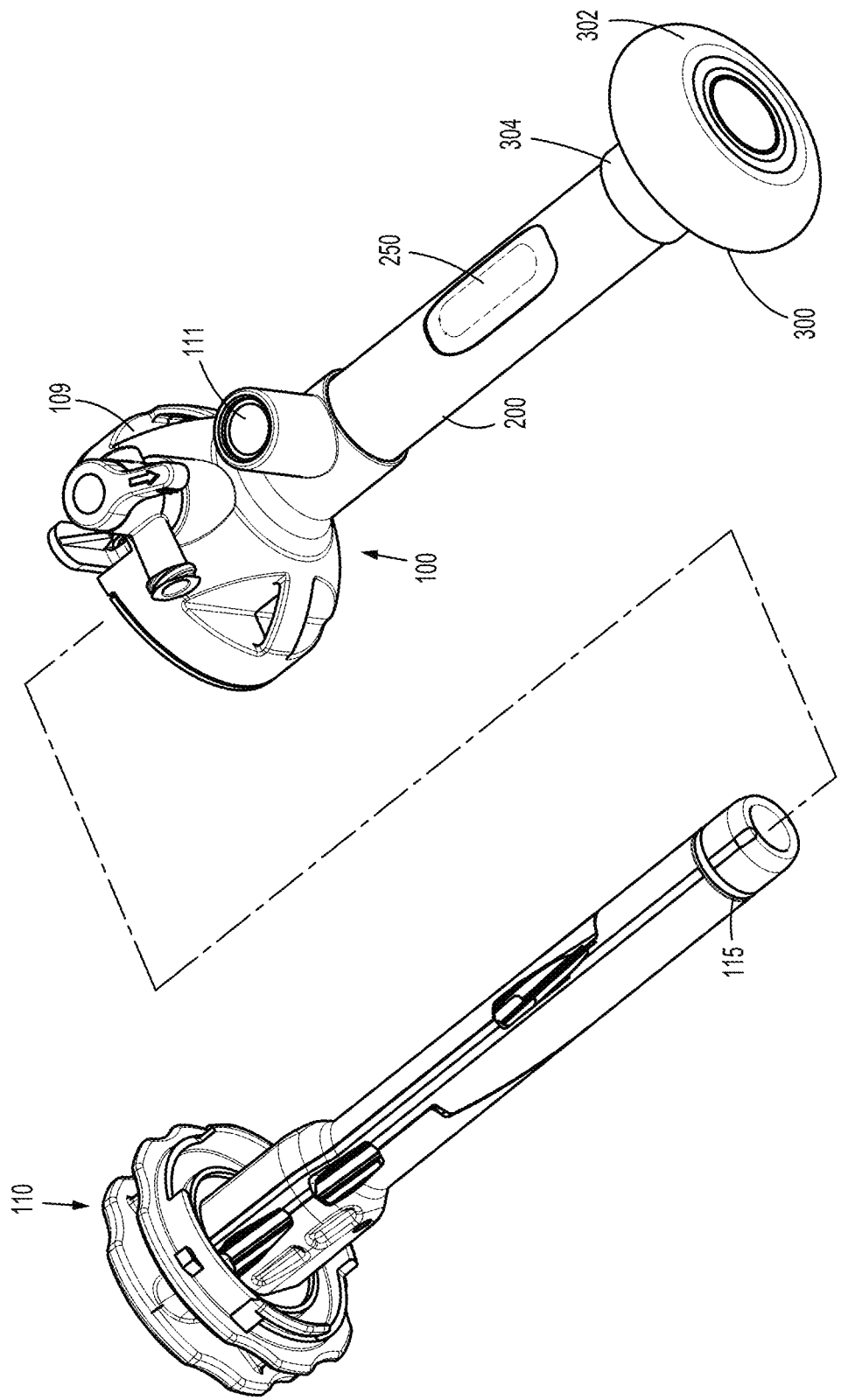
FIG. 1A is a perspective view of the surgical access device of FIG. 1 with a guide separated from a housing of the surgical access device.
Figures 2, 3:
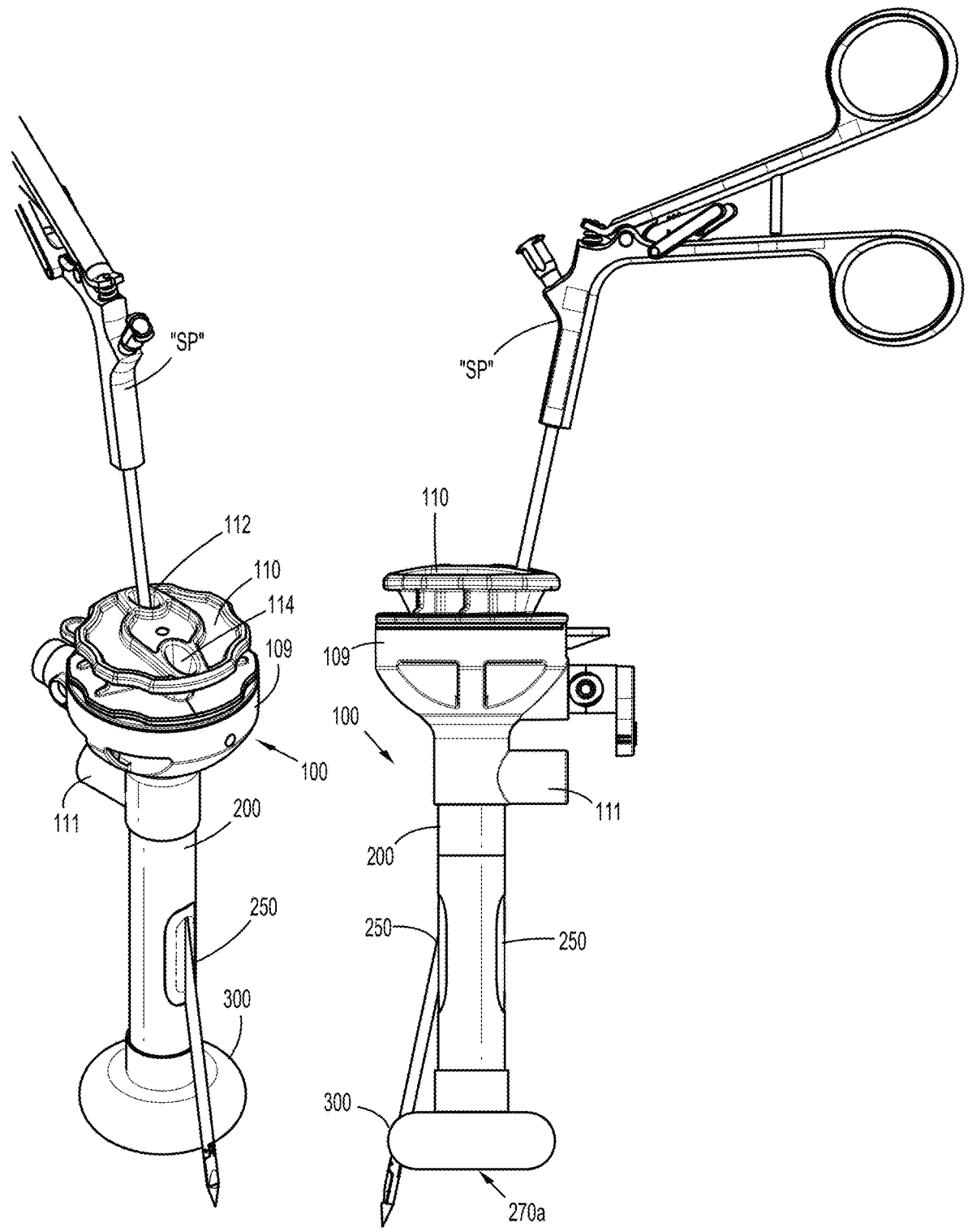
FIG. 2 is a perspective view of the surgical access device of FIG. 1 including a suture passer inserted therethrough.
FIG. 3 is a side view of the surgical access device of FIG. 1 including a suture passer inserted therethrough.

With initial reference to FIGS. 1-3, a surgical access device 100 is shown. Surgical access device 100 includes a housing 109 and a cannula 200 extending distally from housing 109. The cannula 200 defines a longitudinal axis "A-A." A guide or suture guide 110 is attached to or configured to selectively engage the housing 109. The guide has an upper flange and a tube extending from the flange. The guide 110 flange and tube define a first channel 112 and a second channel 114 extending therethrough (FIG. 2), and includes a seal 115 (e.g., an O-ring) (FIG. 1A) on the tube configured to engage an inner wall of cannula 200 for establishing a fluid-tight boundary in the cannula that maintains a pneumoperitoneum in a patient. The access device 100 has an instrument seal housing that is removed from the housing 109 before the guide is attached to the access device 100. The housing 109 includes a zero closure seal, such as a duckbill seal, for sealing the passageway of the cannula when no instrument is inserted through it.

Surgical access device 100 also includes an expandable member or balloon fixation device 300 disposed adjacent a distal end of cannula 200, and at least one slot 250 defined in the cannula 200. As shown in FIGS. 2 and 3, a suture passer "SP" (for example) is insertable through one of channels 112, 114 of guide 110 and through one of slots 250 of cannula 200. Generally, suture passers "SP" are configured to pass a suture through a cannula 200 and to tissue adjacent an incision, for instance.

Additional description of an access device, guide, and suture passer can be found in U.S. Patent Application Publication No. 2015/003879, filed on Jul. 29, 2014, now U.S. Pat. No. 10,258,324, the entire contents of which being hereby incorporated by reference herein. A sealing member is disposed over the slot 250 in the cannula and can be formed from an elastomeric film or tube disposed over the slot 250.

Figure 4:
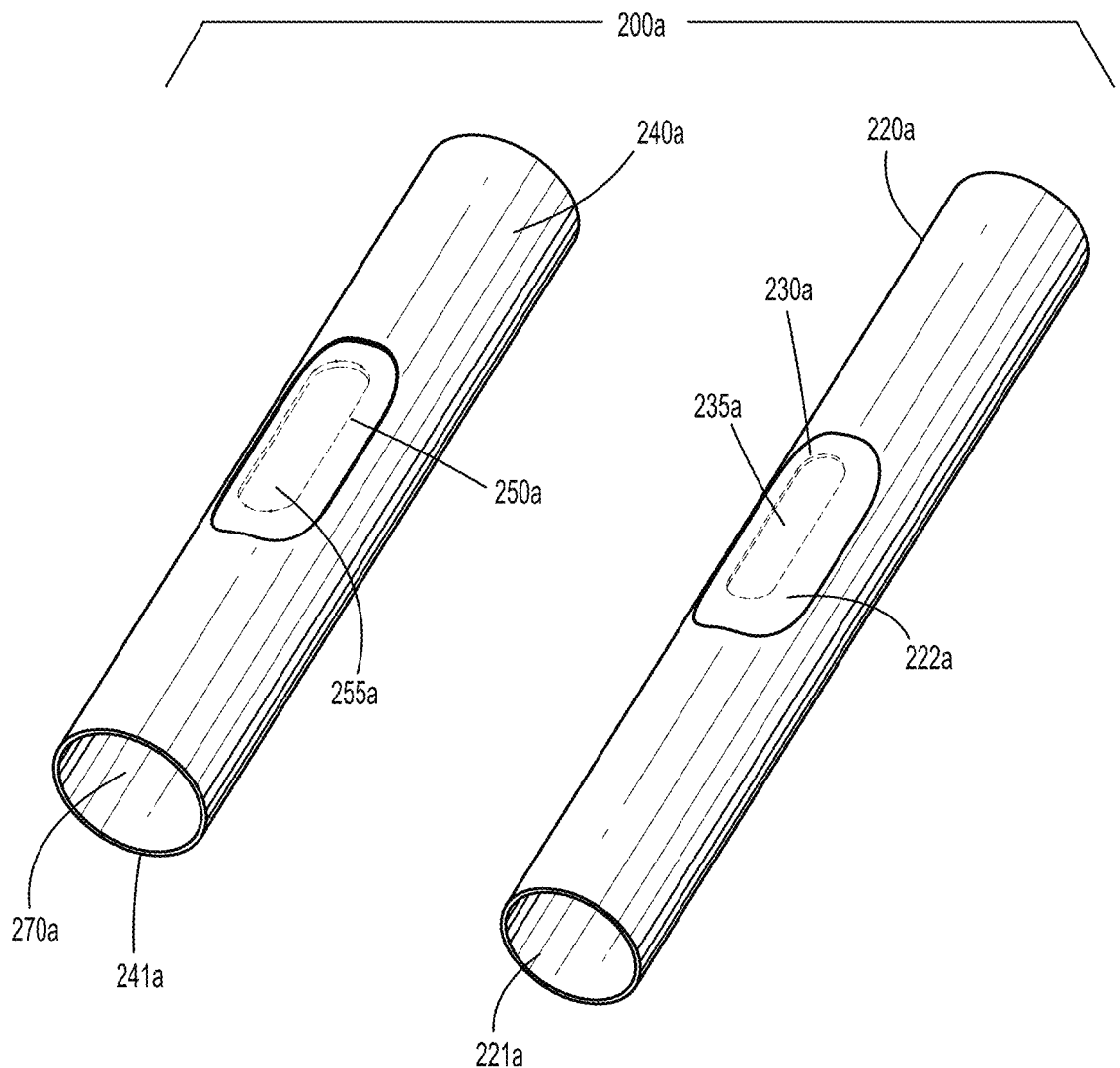
FIG. 4 is a perspective view of an inner tube and an outer tube of the surgical access device of FIGS. 1-3 in accordance with an embodiment of the present disclosure.

Further details of various embodiments of surgical access device 100 are discussed below with reference to FIGS. 4-6. FIG. 4 illustrates an embodiment of a cannula 200a for use with surgical access device 100. Cannula 200a includes an inner tube 220a and an outer tuber 240a. Inner tube 220a is configured to fit within outer tube 240a, and includes at least one slot 230a defined therein. In embodiments, inner tube 220a includes two slots 230a that are 180° offset from each other. In particular, slot 230a is defined by a recessed surface 222a of an outer wall of inner tube 220a. While slot 230a is oval-shaped in the accompanying figures, slot 230a may be any regular or irregular shape, such as circular, rectangular, etc. Further, a film 235a covers slot 230a and may be affixed to recessed surface 222a of inner tube 220a by welding (e.g., ultrasonic welding), for instance, or adhesive bonding. It is envisioned that the outer wall of inner tube 220a and film 235a cooperate to form a flush or nearly flush surface.

With continued reference to FIG. 4, outer tube 240a is configured to fit over inner tube 220a, has a shorter length than inner tube 220a, and includes at least one slot 250a defined therein. As shown in FIG. 3, outer tube 240a includes two slots 250a that are 180° offset from each other. Each slot 250a is shaped to correspond with slot 230a of inner tube 220a, is covered by a film 255a, and is configured to radially and longitudinally align with slot 230a of inner tube 220a when outer tube 240a and inner tube 220a are engaged.

Balloon 300 (FIGS. 1-3) is mounted adjacent a distal end of cannula 200a and is transitionable between a collapsed or deflated configuration and an expanded or inflated configuration. In particular, a distal end 302 of balloon 300 is mounted to or adjacent a distal end 221a of inner tube 220a, and a proximal end 304 of balloon 300 is mounted to or adjacent a distal end 241a of outer tube 240a (FIGS. 1 and 4). In this arrangement, air (or another inflation medium) is forced from an inflation port 111 (FIGS. 1-3), between inner tube 220a and outer tube 240a of cannula 200a, out distal end 241a of outer tube 240a (distal end 241a of outer tube 240 is disposed proximally of distal end 221a of inner tube 220a), and into balloon 300 to inflate balloon 300. To deflate balloon 300, the inflation medium is removed from balloon 300, between inner tube 220a and outer tube 240a of cannula 200a, and out of inflation portion 111. Films 235a and 255a help ensure the air/gas from a pressurized environment within the patient does not escape through inner tube 220a or outer tube 240a of cannula 200a. The balloon can be formed as disclosed in U.S. Pat. No. 10,987,128, the entire disclosure of which is hereby incorporated by reference herein.

In use, a distal portion of cannula 200a is positioned within a patient (e.g., in the abdominal cavity), balloon 300 is inflated through inflation port 111 to help secure cannula 200a with respect to the patient, and a surgical procedure is performed (e.g., by a surgical instrument inserted through a lumen 270a (FIG. 3) of cannula 200a). Following the surgical procedure, the surgical instrument is removed from lumen 270a, and the instrument seal housing is removed from engagement with housing 109, and a portion of guide 110 is inserted through cannula 200a. Next, a suture passer "SP" (FIGS. 2 and 3) is inserted through first channel 112 or second channel 114 of guide 110 and at a non-parallel angle with respect to the longitudinal axis "A-A." Thus, the suture passer "SP" follows a different pathway from the surgical instruments previously used. First channel 112 is angled such that a distal tip of the suture passer "SP" is moved through a neck of balloon 300 and toward slot 230a of inner tube 220a. Urging the suture passer "SP" distally forces the distal tip of the suture passer "SP" to pierce film 235a covering slot 230a of inner tube 220a, to pierce film 255a covering slot 250a of outer tube 240a, and to extend out from the outer tube 240a. Depending on the shape, size and/or orientation of balloon 300, a physician may opt to insert suture passer "SP" into guide 110 and to patient tissue following deflation of balloon 300 to help prevent the distal tip of the suture passer "SP" from interfering with balloon 300. After the distal tip of the suture passer "SP" is positioned at tissue, the suture passer "SP" can be used to suture tissue, or perform a fascial closure. The cannula can include a single slot. In additional embodiments, the cannula 200a includes more than one set of slots, and an additional suture passer or other device can also be inserted through guide 110 (e.g., through channel 114) and through cannula 200a. This can be done while the first suture passer "SP" is at the tissue, or after the first suture passer "SP" has been removed. Thus, the first channel and second channel of the guide 110 is arranged and shaped so that the suture passer is directed toward a particular slot through the cannula when the guide is properly attached to the access device.

FIG. 5 illustrates a further embodiment of a cannula 200b for use with surgical access device 100. Cannula 200b includes an inner tube 220b and an outer tuber 240b. Inner tube 220b is configured to fit within outer tube 240b, and includes at least one slot 230b defined therein. While slot 230b is oval-shaped in the accompanying figures, slot 230b may be any regular or irregular shape, such as circular, rectangular, etc. Inner tube 220b includes a flange 232b surrounding slot 230b. While slot 230b is not covered by a film in the accompanying figures, slot 230b may be covered by a film. Flange 232b (see FIG. 5A) protrudes from inner tube 220b and is configured to engage or nest within a portion of outer tube 240b, as discussed below.

Outer tube 240b is configured to fit over inner tube 220b, has a shorter length than inner tube 220b, and includes at least one slot 250b defined therein. In embodiments, the inner tube 220b includes two slots 250b that are 180° offset from each other to provide further options to the surgeon during fascial closure. Each slot 250b is shaped to correspond with a slot 230b of inner tube 220b, and is configured to radially and longitudinally align with slot 230b of inner tube 220b when outer tube 240b and inner tube 220b are assembled. Additionally, flange 232b of inner tube 220b is configured to nest within slot 250b of outer tube 240b when outer tube 240b and inner tube 220b are engaged. This helps align the inner tube 220b and the outer tube 240b. Thus, only one film is needed for providing an air-tight or nearly air-tight passage. Additionally, cannula 200b can include a balloon 300 or other expandable structure at or adjacent a distal end thereof.

Figure 6:
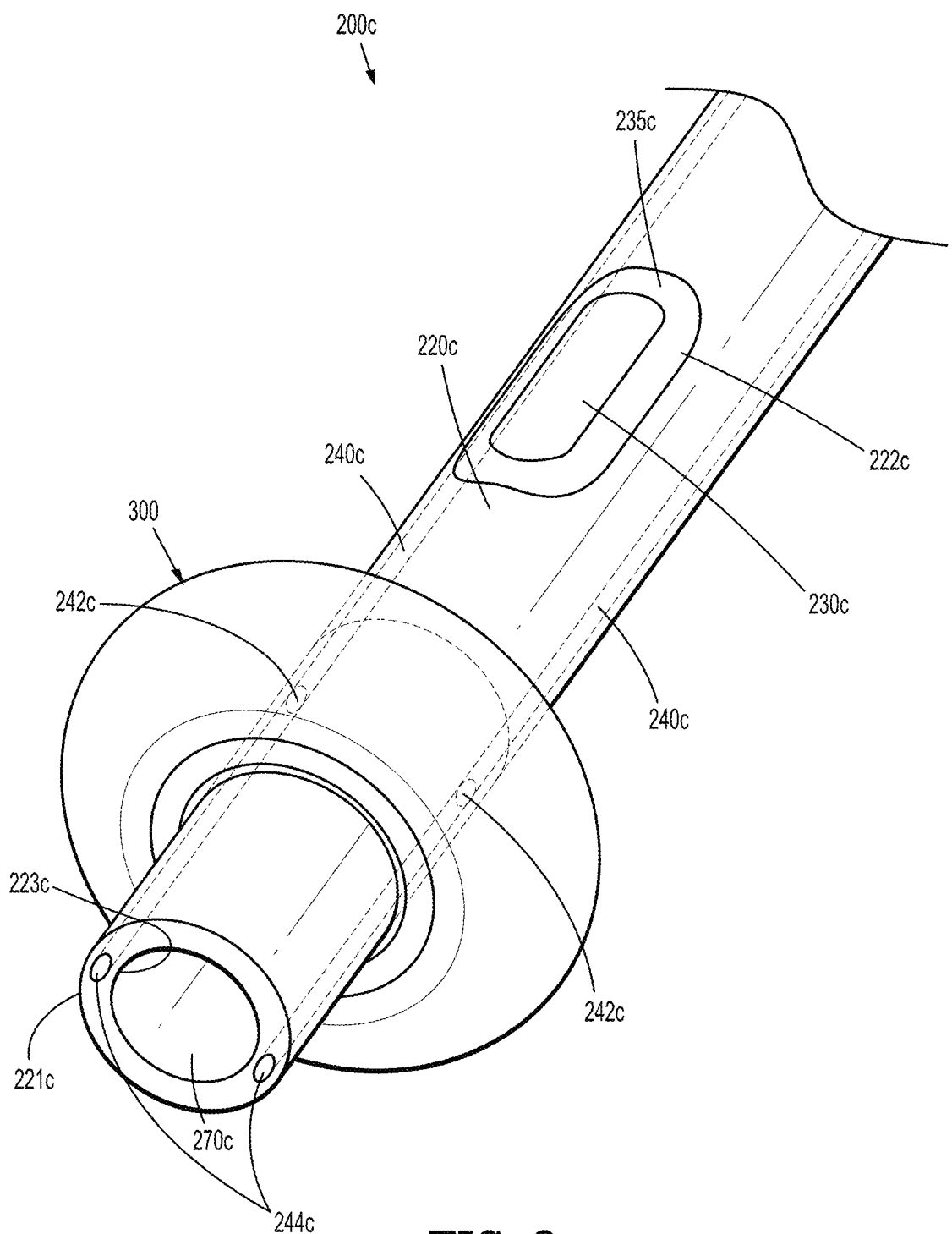
FIG. 6 is a perspective view of a distal end of a cannula of a surgical access device in accordance with another embodiment of the present disclosure.

FIG. 6 illustrates another embodiment of a cannula 200c for use with surgical access device 100. Cannula 200c includes an elongated tube 220c having channels 240c defined within the wall of elongated tube 220c. Elongated tube 220c extends distally from housing 109, and includes at least one slot 230c defined therein. While slot 230c is oval-shaped in the accompanying figures, slot 230c may be any regular or irregular shape, such as circular, rectangular, etc. In particular, slot 230c is defined by a recessed surface 222c of elongated tube 220c. Further, a film 235c covers slot 230c and may be affixed to recessed surface 222c of elongated tube 220c by welding (e.g., ultrasonic welding), for instance, or adhesive bonding. It is envisioned that an outer surface 221c of elongated tube 220c and film 235c cooperate to form a flush or nearly flush surface.

Channels 240c extend along a length (e.g., an entire length) of elongated tube 220c and are defined within the wall of elongated tube 220c. In particular, channels 240c extend between outer surface 221c and an inner surface 223c of elongated tube 220c. Channels 240c are in fluid communication with balloon 300, which is mounted adjacent a distal end of elongated tube 220c, such that when air (or another inflation medium) is forced from inflation port 111 of housing 109 through channels 240c, the air flows out of channel openings 242c into balloon 300 and inflates balloon 300. To deflate balloon 300, the inflation medium is removed from balloon 300, proximally through channels 240c, and out of inflation port 111. Film 235c helps ensure the air/gas from the pressurized environment within the patient does not escape through the wall of elongated tube 220c of cannula 200c.

In embodiments where channels 240c extend an entire length of elongated tube 220c, a distal end 244c of each channel 240c is occluded or blocked to prevent air from escaping therefrom. Including channels 240c that extend an entire length of elongated tube 220c may help optimize manufacturing of cannula 200c. For example, elongated tube 220c can be extruded, and channels 240c extending the length of elongated tube 220c can be formed during the extrusion of elongated tube 220c.

Additionally, in embodiments where cannula 200c includes two channels 240c and two slots 230c, channels 240c and slots 230c may be angularly offset from each other to prevent interference therebetween. For example, channels 240c and slots 230c can be offset by 90° or another suitable angle.

In use, a distal portion of cannula 200c is positioned within a patient (e.g., in the abdominal cavity), balloon 300 is inflated through inflation port 111 to help secure cannula 200c with respect to the patient, and a surgical procedure is performed (e.g., by a surgical instrument inserted through a lumen 270c of cannula 200c). Following the surgical procedure, the surgical instrument is removed from lumen 270c, and the instrument seal housing is removed from engagement with housing 109, and a portion of guide 110 is inserted through cannula 200c. Next, a suture passer "SP" (FIGS. 2 and 3) is inserted through first channel 112 or second channel 114 of guide 110 and at a non-parallel angle with respect to the longitudinal axis "A-A." Thus, the suture passer "SP" follows a different pathway from the surgical instruments previously used. First channel 112 is angled such that a distal tip of the suture passer "SP" is moved toward slot 230c of cannula 200c. Urging the suture passer "SP" distally forces the distal tip of the suture passer "SP" to pierce film 235c covering slot 230c of cannula 200c, and to extend out from the cannula 200c. One or more suture passers "SP" can be used. If cannula 200c includes more than one slot 230c, the slots can be angularly and/or longitudinally offset from one another to accommodate multiple suture passers "SP." The suture passers "SP" deliver suture to tissue at the incision, so the incision can be closed.

Figures 7, 7A:
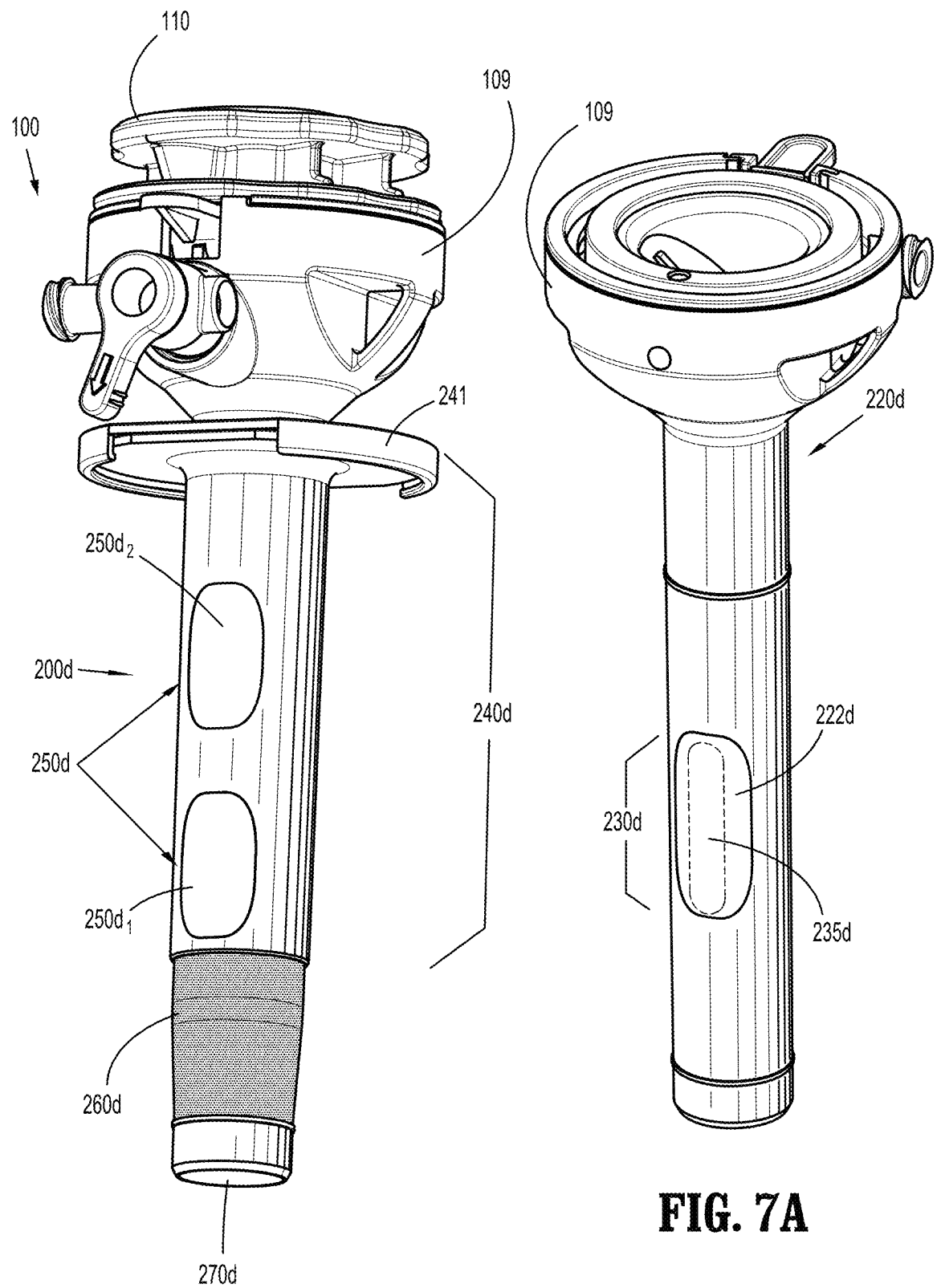
FIG. 7 is a perspective view of a surgical access device including a fixation mesh device in accordance with another embodiment of the present disclosure.
FIG. 7A is a perspective view of an inner tube of the surgical access device of FIG. 7.
Figure 8:
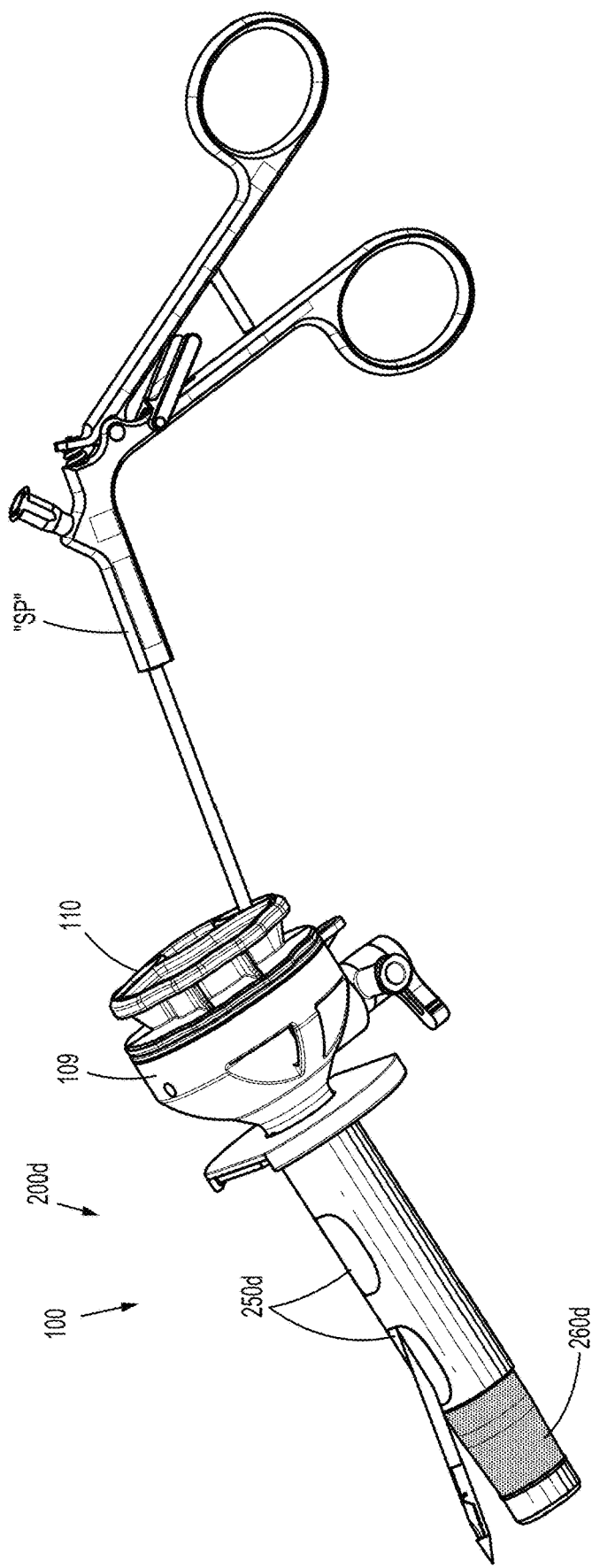
FIG. 8 is a perspective view of the surgical access device of FIG. 7 including a suture passer inserted therethrough.

FIGS. 7-8 illustrate a further embodiment of a cannula 200d for use with surgical access device 100. Cannula 200d includes an inner tube 220d (FIG. 7A), an outer tuber 240d, and a fixation mesh 260d. Inner tube 220d is configured to fit within outer tube 240d, and includes at least one slot 230d defined therein. While slot 230d is oval-shaped in the accompanying figures, slot 230d may be any regular or irregular shape, such as circular, rectangular, etc. In particular, slot 230d is defined by a recessed surface 222d of inner tube 220d. Further, a film 235d covers slot 230d and may be affixed to recessed surface 222d of inner tube 220d by welding (e.g., ultrasonic welding), for instance, or adhesive bonding. It is envisioned that the outer wall of inner tube 220d and film 235d cooperate to form a flush or nearly flush surface. Film 235d helps ensure the insufflation medium (e.g., $CO_2$) from a pressurized environment within the patient does not escape through inner tube 220d of cannula 200d.

Fixation mesh 260d includes a balloon-like cover and is positioned around (e.g., surrounding the walls of) inner tube 220d. The cover can be formed from an elastomeric film. The film can be molded in a shape to encourage the expansion of the mesh member 260d.

Outer tube 240d is configured to fit over inner tube 220d, has a shorter length than inner tube 220d, and includes at least one slot 250d defined therein. Slot 250d is shaped to correspond to slot 230d and is configured to radially and longitudinally align with slot 230d of inner tube 220d when outer tube 240d and inner tube 220d are assembled. Two angularly aligned and longitudinally offset slots 250d are provided, as shown in FIG. 7, and will be discussed in further detail below.

In use, a distal portion of cannula 200d is positioned within a patient (e.g., in the abdominal cavity), fixation mesh 260d is deployed by moving an activation tab 241 distally along the cannula length to expand fixation mesh 260d and to help secure cannula 200d with respect to the patient. In doing this, lower slot $250d_1$ of outer tube 240d moves away from slot 230d of inner tube 220d, and upper slot $250d_2$ of outer tube 240d moves into alignment with slot 230d. A surgical procedure is then performed (e.g., by a surgical instrument inserted through a lumen 270d defined through guide 110 and cannula 200d). Following the surgical procedure, the surgical instrument is removed from lumen 270d, and the instrument seal housing is removed from engagement with housing 109, and a portion of guide 110 is inserted through cannula 200d. Next, a suture passer "SP" (FIGS. 2 and 3) is inserted through first channel 112 or second channel 114 of guide 110 and at a non-parallel angle with respect to the longitudinal axis "A-A." Thus, the suture passer "SP" follows a different pathway from the surgical instruments previously used. First channel 112 is angled such that a distal tip of the suture passer "SP" is moved toward slot 230d of inner tube 220d. Urging the suture passer "SP" distally forces the distal tip of the suture passer "SP" to pierce film 235d covering slot 230d of inner tube 220d, and extend through slot 250d of outer tube 240d. Depending on the shape, size and/or orientation of fixation mesh 260d, a physician may opt to insert suture passer into patient following the movement of fixation mesh 260d to its pre-deployed or undeployed position to help prevent the distal tip of the suture passer from interfering with a deployed portion of fixation mesh 260d. After the distal tip of the suture passer is positioned at tissue, the suture passer can be used to perform a fascial closure. The suture passer can extend through slot 230d and slot $250d_1$ when fixation mesh 260d is not deployed, or through slot 230d and slot $250d_2$ when fixation mesh 260d is deployed.

In some embodiments, inner tube 220d and outer tube 240d of cannula 200d include more than one angularly offset sets of slots to accommodate more than one suture passer.

Figure 9:
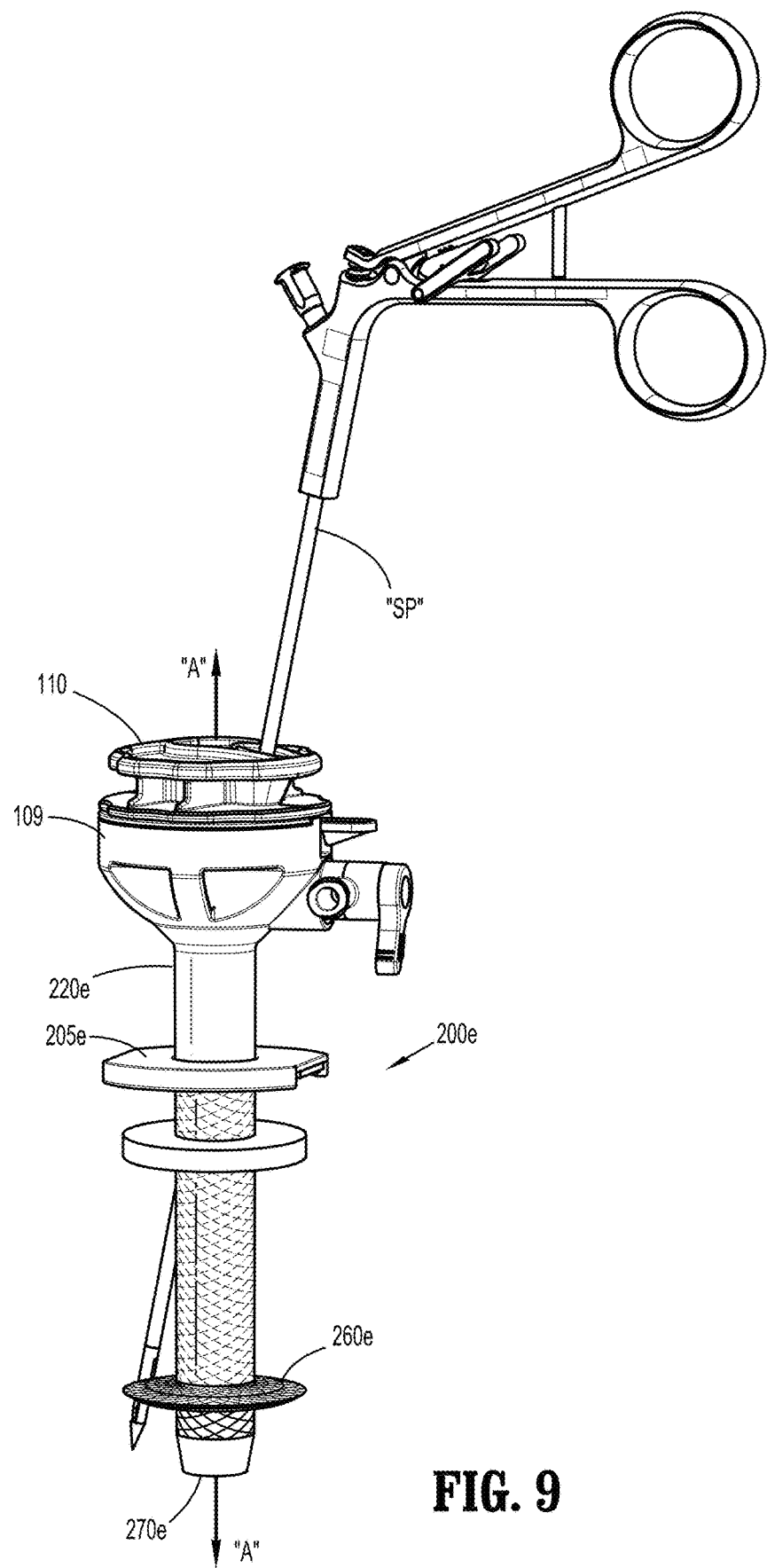
FIG. 9 is a perspective view of a surgical access device in accordance with another embodiment of the present disclosure including a suture passer extending therethrough and illustrating a fixation mesh in a deployed configuration.
Figure 10:
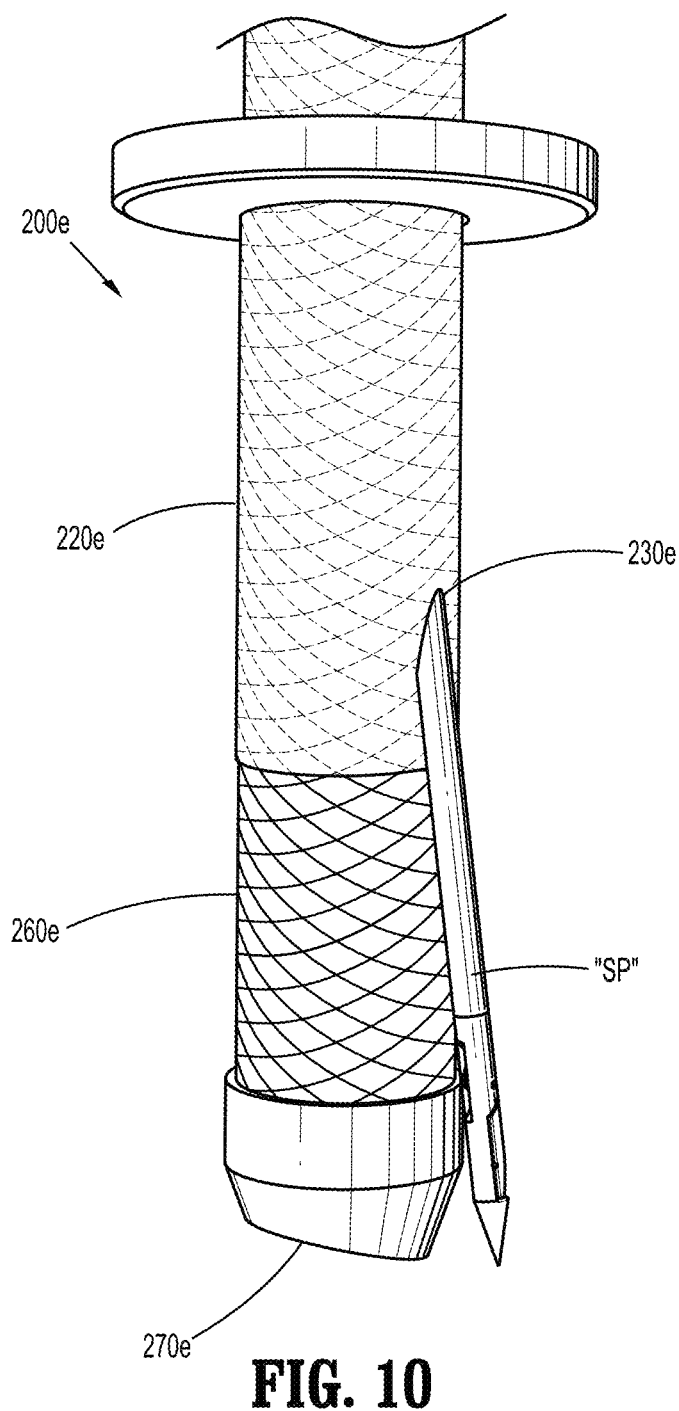
FIG. 10 is a side view of a distal end of the surgical access device and suture passer of FIG. 9 illustrating the fixation mesh in an undeployed configuration.

FIGS. 9 and 10 illustrate another embodiment of a cannula 200e for the surgical access device 100. Cannula 200e includes an elongated tube 220e, and a fixation mesh 260e. Elongated tube 220e includes at least one slot 230e (e.g., an oval-, round-, rectangular-, or other-shaped slot) defined therein. In contrast to the embodiment of cannula 200d discussed above with regard to FIGS. 7 and 8, slot 230e is not covered by a film, but a film may be provided in other embodiments.

Fixation mesh 260e can include a balloon-like cover and is positioned around (e.g., surrounding the wall of) elongated tube 220e. Further, fixation mesh 260e covers a substantial portion of the length of cannula 200e, and can be adhered or affixed to a flange 205e of cannula 200e in an air-tight manner to provide an air-tight seal therebetween. In this regard, fixation mesh 260e helps ensure the air/gas from a pressurized environment within the patient does not escape through elongated tube 220e of cannula 200e.

In use, a distal portion of cannula 200e is positioned within a patient (e.g., in the abdominal cavity), fixation mesh 260e is deployed by moving flange 205e distally along the cannula length. This expands fixation mesh 260e to help secure cannula 200e with respect to the patient. A surgical procedure is performed (e.g., by a surgical instrument inserted through a lumen 270e defined through guide 110 and cannula 200e). Following the surgical procedure, the surgical instrument is removed from lumen 270e, and the instrument seal housing is removed from engagement with housing 109, and a portion of guide 110 is inserted through cannula 200d. Next, a suture passer "SP" (FIGS. 2 and 3) is inserted through first channel 112 or second channel 114 of guide 110 and at a non-parallel angle with respect to the longitudinal axis "A-A." Thus, the suture passer "SP" follows a different pathway from the surgical instruments previously used. First channel 112 is angled such that a distal tip of the suture passer "SP" is moved adjacent slot 230e of elongated tube 220e at a non-parallel angle with respect to the longitudinal axis "A-A." Urging the suture passer "SP" distally forces the distal tip of the suture passer "SP" to pierce fixation mesh 260e, and to thereby extend out from cannula 200e. A physician may opt to insert suture passer "SP" into patient following the movement of fixation mesh 260e to its pre-deployed or undeployed position or may pass the suture passer through fixation mesh 260e while it is in the deployed state. After the distal tip of the suture passer "SP" is positioned within tissue, the suture passer "SP" can be used to perform a fascial closure or other closure or suturing of tissue. Additionally, in embodiments where elongated tube 220e of cannula 200e includes more than one angularly offset slot, a second suture passer can also be inserted through cannula 200e.

The present disclosure also includes methods of performing a surgical procedure including using the fixation device (e.g., inflatable member 300 or fixation mesh 260d, 260e) to secure the surgical access device 100 within tissue, performing a surgical procedure through the cannula, removing a seal housing from housing 109, mounting guide 100 to housing 109, inserting a distal portion of a suture passer through channel 112, 114 of guide 110 and through a slot in the cannula 200, and performing a fascial closure or other procedure on tissue. As noted above, depending on the particular embodiment of the surgical access device 100, the fixation device can remain inflated/deployed during the fascial closure, or the fixation device can be deflated/undeployed while the fascial closure is performed.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical access device, comprising:
a housing;
a cannula extending distally from the housing and defining a longitudinal axis, the cannula including a wall defining a first slot;
a guide engagable with the housing and defining a first channel that is disposed at a non-parallel angle relative to the longitudinal axis; and
a lumen extending through the housing, through the cannula, and through the guide, the lumen being coaxial with the longitudinal axis while the guide is engaged with the housing,
wherein a first surgical instrument is insertable through the first channel of the guide and through the first slot of the cannula.

2. The surgical access device according to claim 1, wherein the wall of the cannula defines a second slot.

3. The surgical access device according to claim 2, wherein the first slot of the cannula is disposed at a first distance along the longitudinal axis from the housing, the second slot of the cannula is disposed at a second distance along the longitudinal axis from the housing, the second distance is greater than the first distance.

4. The surgical access device according to claim 2, wherein each of the first slot and the second slot is completely bound by the wall of the cannula.

5. The surgical access device according to claim 1, wherein the first slot is completely bound by the wall of the cannula.

6. The surgical access device according to claim 1, wherein an entirety of the lumen is coaxial with the longitudinal axis.

7. The surgical access device according to claim 1, wherein the first channel includes a proximal end, the housing includes a proximal end, and the proximal end of the first channel extends through the proximal end of the housing.

8. The surgical access device according to claim 1, further including a channel disposed within the wall of the cannula, the cannula including a proximal portion and a distal portion, the channel extending between the proximal portion of the cannula and the distal portion of the cannula.

9. A surgical access device, comprising:
a cannula defining a longitudinal axis, the cannula including a proximal portion, a distal portion, and a wall defining a first slot;
a guide disposed in mechanical cooperation with the cannula, the guide defining a first channel that is disposed at a non-parallel angle relative to the longitudinal axis; and
a lumen extending through the cannula, and through the guide, the lumen being coaxial with the longitudinal axis while the guide is in mechanical cooperation with the cannula,
wherein a first surgical instrument is simultaneously insertable through the first channel of the guide and through the first slot of the cannula.

10. The surgical access device according to claim 9, further having an expandable member disposed adjacent the distal portion of the cannula, the expandable member transitionable between a collapsed configuration and an expanded configuration.

11. The surgical access device according to claim 10, wherein the expandable member includes a fixation mesh.

12. The surgical access device according to claim 9, wherein the wall of the cannula is formed from an inner tube and an outer tube.

13. The surgical access device according to claim 12, further having an expandable member disposed adjacent the distal portion of the cannula, the expandable member being a mesh member that expands upon movement of the outer tube distally from a first position to a second position relative to the inner tube.

14. The surgical access device according to claim 9, wherein an entirety of the lumen is coaxial with the longitudinal axis.

15. The surgical access device according to claim 9, wherein the wall of the cannula defines a second slot.

16. The surgical access device according to claim 15, wherein the first slot of the cannula is disposed at a first distance along the longitudinal axis from the guide, the second slot of the cannula is disposed at a second distance along the longitudinal axis from the guide, the second distance is greater than the first distance.

17. The surgical access device according to claim 15, wherein each of the first slot and the second slot is completely bound by the wall of the cannula.

18. The surgical access device according to claim 9, wherein the first slot is completely bound by the wall of the cannula.

19. The surgical access device according to claim 9, further including a housing disposed adjacent the proximal portion of the cannula, wherein the guide is engageable with the housing.

20. A surgical access device, comprising:
a housing;
a cannula extending distally from the housing and defining a longitudinal axis, the cannula including a wall defining a first slot, the cannula including an inner tube and an outer tube;
a guide engagable with the housing and defining a first channel that is disposed at a non-parallel angle relative to the longitudinal axis; and
a lumen extending through the housing, through the cannula, and through the guide, the lumen being coaxial with the longitudinal axis,
wherein a first surgical instrument is insertable through the first channel of the guide and through the first slot of the cannula.

* * * * *